US010022428B2

(12) United States Patent
Chuang et al.

(10) Patent No.: US 10,022,428 B2
(45) Date of Patent: Jul. 17, 2018

(54) MARKER FOR ACID SPHINGOMYELINASE DISORDERS AND USES THEREOF

(71) Applicant: Genzyme Corporation, Cambridge, MA (US)

(72) Inventors: Wei-Lien Chuang, Bridgewater, NJ (US); Gerald F. Cox, Bridgewater, NJ (US); X. Kate Zhang, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 14/895,472

(22) PCT Filed: Jun. 6, 2014

(86) PCT No.: PCT/US2014/041405
§ 371 (c)(1),
(2) Date: Dec. 2, 2015

(87) PCT Pub. No.: WO2014/197859
PCT Pub. Date: Dec. 11, 2014

(65) Prior Publication Data
US 2016/0120958 A1    May 5, 2016

Related U.S. Application Data

(60) Provisional application No. 61/832,302, filed on Jun. 7, 2013.

(51) Int. Cl.
*A61K 38/30* (2006.01)
*A61K 38/46* (2006.01)
*G01N 33/92* (2006.01)

(52) U.S. Cl.
CPC .......... *A61K 38/465* (2013.01); *G01N 33/92* (2013.01); *C12Y 301/04012* (2013.01); *G01N 2333/922* (2013.01); *G01N 2405/08* (2013.01); *G01N 2800/04* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,039,388 A | 8/1977 | Gal et al. | |
| 4,082,781 A | 4/1978 | Gal | |
| 5,686,240 A | 11/1997 | Schuchman et al. | |
| 6,541,218 B1 * | 4/2003 | Schuchman | A01K 67/0278 435/183 |
| 7,001,994 B2 | 2/2006 | Zhu | |
| 7,563,591 B2 | 7/2009 | Chamoles | |
| 9,655,954 B2 * | 5/2017 | Schuchman | C12Y 301/0401 |
| 2009/0286272 A1 | 11/2009 | Ory et al. | |
| 2011/0052559 A1 | 3/2011 | Schuchman et al. | |

FOREIGN PATENT DOCUMENTS

| | | | |
|---|---|---|---|
| CN | 102596232 | 7/2012 | |
| JP | 2006-214731 | 8/2006 | |
| WO | WO-2006/058385 | 6/2006 | |
| WO | WO-2007/078806 | 7/2007 | |
| WO | WO-2011/025996 | 3/2011 | |
| WO | WO-2013/072060 | 5/2013 | |
| WO | WO 2013/072060 A2 * | 5/2013 | ............. G01N 33/68 |

OTHER PUBLICATIONS

Rodriguez-Lafrasse et al., Neurochem Res, 24(2):199-205, Feb. 1999.*
OMIM entry 607608, Sphingomyelin phosphodiesterase 1, acid lysosomal; SMPD1. Published Mar. 11, 2010 [online]. Retrieved from <http://omim.org/entry/607608>. Retrieved on Nov. 22, 2016.*
ClinicalTrials.gov Identifier NCT01722526, Published Nov. 5, 2012 [online] Retrieved from <https://www.clinicaltrials.gov/ct2/show/NCT01722526?term=NCT01722526&rank=1> Retrieved on Nov. 22, 2016.*
Miranda et al, FASEB J. 14 (13):1988-1995, 2000.*
Lyso-Sphingomyelin, Caymen Chemical Co. Item No. 10007947, available at https://www.caymanchem.com/app/template/Product.vm/catalog/10007947, 4 pages.
Chuang et al., "Lyso-sphingmyelin is elevated in dried blood spots of Niemann-Pick B pati," Mol Genet Metab (2014) 11(2):209-211.
Clair et al., "Autotaxin hydrolyzes sphingosylphosphorylcholine to produce the regulator of migration, sphingosine-1-phosphate," Cancer Res (2003) 63(17):5446-5453.
Galbiati et al., "Combined hematopoietic and lentiviral gene-transfer therapies in newborn twitcher mice reveal contemporaneous neurodegeneration and demyelination in Krabbe disease," J Neurosci Res (2009) 87(8):1748-1759.
He et al., "Characterization of human acid sphingomyelinase purified from the media of overexpressing Chinese hamster ovary cells," Biochim Biophys Acta (1999) 1432(2):251-264.
Horinouchi et al., "Acid sphingomyelinase deficient mice: a model of types A and B Niemann-Pick disease," Nature Genetics (1995) 10:288-293.
International Preliminary Report on Patentability for PCT/US2014/041405, dated Dec. 17, 2015, 11 pages.
International Search Report and Written Opinion for PCT/US2014/041405, dated Sep. 24, 2014, 15 pages.
Ito et al., "A novel enzyme that cleaves the N-acyl linkage of ceramides in various glycosphingolipids as well as sphingomyelin to produce their lyso forms," J Biol Chem (1995) 270(41):24370-24374.
McGovern et al., "A phase 1 trial of recombinant human acid sphingomyelinase (rhASM) enzyme replacement therapy in adults (Continued)

*Primary Examiner* — Kimberly Ballard
*Assistant Examiner* — Stacey N MacFarlane
(74) *Attorney, Agent, or Firm* — Steptoe & Johnson LLP; Z. Ying Li; Siew Y. Chong

(57) ABSTRACT

The present disclosure provides methods of screening, diagnosing, monitoring and/or treating acid sphingomyelinase (ASM) disorders such as Niemann-Pick disease. In particular, the methods encompass techniques for improved diagnosis and/or treatment of an ASM disorder, for example using enzyme replacement therapy.

39 Claims, 4 Drawing Sheets

(56) References Cited

OTHER PUBLICATIONS with Asm deficiency (Asmd)," (2012) Retrieved from the Internet: URL: http://www.nnpdf.org/documents/neimannpickposterICIEMO9FINAL.pdf.

Meikle et al., "Prevalence of lysosomal storage disorders," JAMA (1999) 281(3):249-254.

Miranda et al., "Infusion of recombinant human acid sphingomyelinase into Niemann-Pick disease mice leads to visceral, but not neurological, correction of the pathophysiology," FASEB J (2000) 14(13):1988-1995.

Murata et al., "Abnormal expression of sphingomyelin acylase in atopic dermatitis: an etiologic factor for ceramide deficiency," J Invest Dermatol (1996) 106(6):1242-1249.

Pentchev et al., "The isolation and characterization of sphingomyelinase from human placental tissue," Biochim Biophys Acta (1977) 488(2):312-321.

Pinto et al., "Prevalence of lysosomal storage diseases in Portugal," Eur J Hum Genet (2004) 12(2):87-92.

Poorthuis et al., "The frequency of lysosomal storage disease in the Netherlands," Hum Genet (1999) 105(1-2):151-156.

Quintern et al., "Acid sphingomyelinase from human urine: purification and characterization," Biochim Biophys Acta (1987) 922(3):323-336.

Savic et al., "Use of acid sphingomyelinase for cancer therapy," Adv Cancer Res (2013) 117:91-115.

Simonaro et al., "The Demographics and Distribution of Type B Niemann-Pick Disease: Novel Mutations Lead to New Genotype/Phenotype Correlations," Am J Hum Genet (2002) 71(6):1413-1419.

Smith et al., "The unexpected role of acid sphingomyelinase in cell death and the pathophysiology of common diseases," FASEB J 22(10):3419-3431.

Tokumura et al., "Identification of human plasma lysophospholipase D, a lysophosphatidic acid-producing enzyme, as autotaxin, a multifunctional phosphodiesterase," J Biol Chem (2002) 277(42):39436-39442.

Wasserstein et al., "Acid sphingomyelinase deficiency: Prevalence and characterization of an intermediate phenotype of Niemann-Pick Disease," J Pediatr (2006) 149(4):554-559.

Yamanaka et al., "Acid sphingomyelinase of human brain: purification to homogeneity," J Neurochem (1982) 38:1753-1764.

Communication pursuant to Rules 161(1) and 162 EPC for EP 14735056.5, dated Feb. 12, 2016, 2 pages.

Liliom et al., "Sphingosylphosphocholine is a naturally occurring lipid mediator in blood plasma: a possible role in regulating cardiac function via sphingolipid receptors," Biochem J. (2001) 355(Pt. 1):189-197.

Nixon et al. "The multi-functional role of sphingosylphosphorylcholine," Progress in Lipid Research (2008) 47:63-75.

Giese et al., "A novel, highly sensitive and specific biomarker for Niemann-Pick type C1 disease," Orphanet Journal of Rare Disease (2015) 10:78.

Merrill, Jr. and Sandhoff, "Sphingolipids: metabolism and cell signaling." In "Biochemistry of Lipids, Lipoproteins and Membranes," edited by D.E. Vance and J.E. Vance, Chapter 14, pp. 373-407. 4th Ed., 2002.

* cited by examiner

MARKER FOR ACID SPHINGOMYELINASE DISORDERS AND USES THEREOF

This application is a U.S. national phase application of International Application No. PCT/US2014/041405 having the international filing date of Jun. 6, 2014, entitled "MARKER FOR ACID SPHINGOMYELINASE DISORDERS AND USES THEREOF," which claims the benefit of priority under 35 U.S.C. § 119 of U.S. Provisional Application No. 61/832,302, filed Jun. 7, 2013. The contents of the above applications are incorporated herein by reference in their entireties for all purposes.

The present disclosure relates to methods of screening, diagnosing, monitoring and/or treating acid sphingomyelinase (ASM) disorders such as Niemann-Pick disease.

Acid sphingomyelinase (ASM) is a lysosomal phosphodiesterase enzyme that hydrolyzes sphingomyelin (SPM), a phospholipid storage substance found in the brain, liver, lungs, spleen and lymph nodes, to ceramide and phosphorylcholine. Loss of ASM activity can result in the inability of the body to break down SPM. In patients with ASM disorders, SPM accumulates predominantly in macrophages, but also within hepatocytes and other cell types, resulting in marked hepatosplenomegaly, thrombocytopenia, interstitial lung disease, and coronary artery disease. SPM is not significantly elevated in plasma, whole blood, or urine, rendering it of limited use as a non-invasive biomarker.

Diagnosis of an ASM disorder currently requires invasive testing and/or time-consuming medical examination, such as an evaluation of suspected clinical signs and symptoms, liver or lung biopsy, testing for ASM activity in a blood sample (where false negative and positive cases have been reported), and/or genetic testing (e.g., SMPD1 gene mutation analysis). Treatment of ASM disorders can include administration of replacement enzyme. At high doses, enzyme replacement therapy can result in the production of toxic or harmful metabolites. Accordingly, there is a need to develop improved methods for screening, diagnosing and/or monitoring the course of treatment for an ASM disorder. Disclosed herein are methods of non-invasively screening, diagnosing, monitoring therapy, and/or adjusting the dose of a therapeutic agent for treating an ASM disorder, comprising measuring the level of lyso-SPM (sphingosylphosphorylcholine or lyso-sphingomyelin) in a biological sample. Elevated levels of lyso-SPM can be used to screen for or diagnose an ASM disorder. Elevated levels of lyso-SPM can also be used as a signal or indication of the production of one or more toxic metabolites associated with an excessively high dose of enzyme replacement therapy, thereby allowing for the calibration of enzyme therapy to reduce the buildup of SPM while avoiding harmful side-effects of the therapy. Elevated levels of lyso-SPM can also be used to monitor the long-term efficacy of a course of treatment for an ASM disorder (e.g., if levels of lyso-SPM do not decrease over the course of treatment, this can indicate an ineffective treatment).

Niemann-Pick disease (NPD) is an inherited, autosomal recessive lipid storage disorder characterized by excessive accumulation of SPM in the lysosomes of cells such as macrophages and neurons, which impairs normal cellular function. Niemann-Pick Type A ("NPD-A") is a rapidly progressive neurodegenerative disease in infants and typically results in death within two to three years of age. Niemann-Pick Type B ("NPD-B") results in the enlargement of the liver and spleen, and respiratory distress with death generally ensuing by early adulthood. Other types of Niemann-Pick disease, e.g., Type C ("NPD-C"), may also be associated with accumulation of SPM and/or lyso-SPM. They are also referred to herein as ASM disorders (ASMD). These forms of Niemann-Pick disease are collectively referred to herein as Niemann-Pick disease (NPD).

NPD occurs more frequently among individuals of Ashkenazi Jewish ancestry than in the general population. It is estimated that the incidence of NPD-A among Ashkenazi Jews is about 1 in 40,000, with a gene frequency (q) of about 1 in 200 and a heterozygote carrier frequency (2 pq) of 1 in 100 (Goodman, 1979, in "Genetic Disorders Among The Jewish People", John Hopkins Univ. Press, Baltimore, pp. 96-100). The heterozygote carrier incidence of NPD-B in the Ashkenazi Jewish population is less frequent. Id. The combined heterozygote carrier frequency for NPD A and B has been estimated to be about 1 in 70 among individuals of Ashkenazi Jewish decent. Id. In epidemiologic studies conducted in various countries, the combined incidence of NPD A and B disease in several countries in the world is estimated to range from 1 in 167,000 to 1 in 250,000 newborns (Miekle et al., 1999 JAMA 281(3):249-254; Poorthuis et al., 1999 Hum. Genet. 105:151-156; Pinto et al., 2004 Euro. J. Hum. Gene. 12:87-92). The heterozygote carrier rate is believed to range from 1 in 200 to 1 in 250 individuals.

Patients with either NPD-A or NPD-B have residual ASM activity (about 1 to 10% of normal), but this is not sufficient to prevent the excessive accumulation of sphingomyelin in the lysosomes. Moreover, the clinical course of NPD-B is highly variable, and it is not presently possible to correlate disease severity with the level of residual ASM activity. Although the enzymatic diagnosis of affected patients with either NPD-A or NPD-B can be made in blood samples, this diagnosis is often preceded by invasive procedures such as liver or lung biopsy. In addition, the enzymatic detection of obligate heterozygotes has proven problematic, particularly using peripheral leukocytes as the enzyme source. One possibility is that the occurrence of neutral sphingomyelinases in some sources and/or the presence of residual ASM activity resulting from the mutant alleles have contributed to the inability to reliably discriminate carriers for either disease subtype. Even the use of cultured skin fibroblasts, which do not express the neutral sphingomyelinase, has not provided unambiguous results with heterozygotes. Accordingly, alternative methods for accurately detecting, screening, diagnosing, and treating ASM disorders, such as NPD, are needed.

Enzyme replacement therapy (ERT) has been used to treat various lysosomal storage diseases. See, e.g., U.S. Pat. No. 7,001,994 and U.S. Patent Application No. 2011/0052559, discussing ERT for Tay-Sachs, Pompe, and Niemann-Pick disease, among others, which are incorporated herein in their entirety. ERT attempts to supplement the deficient and/or defective enzyme with exogenously supplied enzyme. In the case of ERT for Niemann-Pick disease, the goal would be to enable the affected individual to process sphingomyelin and avoid its buildup within the lysosomes. To be effective, such therapy can initially require a sufficiently large amount of the replacement enzyme to break down the accumulated sphingomyelin, as well as continued administration of replacement enzyme to avoid subsequent re-accumulation of sphingomyelin. The metabolism of accumulated sphingomyelin can, however, result in the production of toxic or harmful metabolites. Careful coordination of ERT is needed, therefore, to effectively debulk accumulated sphingomyelin in a patient without producing elevated levels of metabolite that may result in adverse side effects.

As noted previously, SPM is not significantly elevated in plasma, whole blood, or urine, rendering it of limited use as a non-invasive biomarker to screen, diagnose or monitor treatment for an ASM disorder. As disclosed herein, lyso-SPM (sphingosylphosphorylcholine or lyso-sphingomyelin), the deacylated form of SPM, is significantly elevated in tissues, including peripheral tissues, in patients suffering from and/or being treated for ASM disorders, making it a potential marker for screening, diagnosing, and/or monitoring treatment for an ASM disorder. This dichotomy is in contrast to many other lysosomal storage disorders, where altered levels of both the acylated and deacylated glycosphingolipids are detectable in plasma. Given that altered levels of SPM are not detectable in plasma from patients suffering from or being treated for ASM disorders, it might have been expected that lyso-SPM would likewise not be suitable for screening, diagnosis, or monitoring of treatment. However, as disclosed herein, it has been found that lyso-SPM can be detected at altered levels in biological samples from various tissues, including peripheral tissues such as blood plasma.

Lyso-sphingolipids (lyso-SL), which include lyso-SPM, are the deacylated forms of sphingolipids; several have been shown to be elevated in certain lysosomal storage disorders. Galbiati et al., "Combined hematopoietic and lentiviral gene-transfer therapies in newborn Twitcher mice reveal contemporaneous neurodegeneration and demyelination in Krabbe disease," *J. Neurosci. Res.* 87: 1748-1759 (2009). The mechanism by which lyso-SPM and other lyso-SL are produced has not been fully elucidated. The lack of a concurrent elevation in sphingosine suggests that deacylation of the corresponding sphingolipid is the likely route of generation. However, the only sphingomyelin deacylase identified to date is from the stratum corneum of an atopic dermatitis subject. Murata et al., "Abnormal expression of sphingomyelin acylase in atopic dermatitis: an etiologic factor for ceramide deficiency?", *J. Invest. Dermatol.* 106: 1242-1249 (1996). The expression of this deacylase appears to be limited to selected cell types under certain physiological conditions. Purified ASM from placenta, brain, and urine has been shown not to hydrolyze lyso-SPM. Pentchev et al., "The isolation and characterization of sphingomyelinase from human placental tissue," *Biochim. Biophys. Acta.* 488: 312-321 (1977); Yamanaka and Suzuki, "Acid sphingomyelinase of human brain: purification to homogeneity," *J. Neurochem.* 38: 1753-1764 (1982); Quintern et al., "Acid sphingomyelinase from human urine: purification and characterization," *Biochim. Biophys. Acta.* 922: 323-336 (1987). The lack of understanding regarding the biosynthetic pathway for lyso-SPM further emphasizes the difficulty in predicting its expression level a priori in patients suffering from ASM disorders.

Lyso-SPM has a short half-life in blood in vitro because of its rapid metabolism to sphingosine-1-phosphate through autotaxin, an exoenzyme with lysophospholipase D activity. Tokumura et al., "Identification of human plasma lysophospholipase D, a lysophosphatidic acid-producing enzyme, as autotaxin, a multifunctional phosphodiesterase," *J. Biol. Chem.* 277: 39436-39442 (2002); Clair et al., "Autotaxin hydrolyzes sphingosylphosphorylcholine to produce the regulator of migration, sphingosine-1-phosphate," *Cancer Res.* 63: 5446-5453 (2003). Other than in spleen and liver of NPD-B patients, and the brains of NPD-A subjects who have little to no ASM activity and manifest severe neuropathic disease, there are no reports on the level of lyso-SPM in other organs.

As disclosed herein, lyso-SPM can be detected at altered concentrations in biological samples (e.g., samples taken from peripheral tissues) from patients suffering from and/or being treated for ASM disorders. The altered level can reflect a transient effect of treatment (e.g., altered lyso-SPM levels can serve as a marker for the production of acute toxic metabolites in response to ERT). The altered levels can also be used diagnostically (e.g., altered lyso-SPM levels can serve as a diagnostic or screening marker to identify a symptomatic or pre-symptomatic subject suffering from an ASM disorder). The altered levels can also be used to monitor the long-term efficacy of a course of treatment for an ASM disorder (e.g., if levels of lyso-SPM do not decrease over the course of treatment, this can indicate an ineffective treatment). Accordingly, disclosed herein are new methods of screening, diagnosing, monitoring the progression of treatment, and/or adjusting the dose of a therapeutic agent for treating an ASM disorders such as NPD using novel biomarkers including lyso-SPM (sphingosylphosphorylcholine or lyso-sphingomyelin). Monitoring the course of treatment can include detecting a reduction in the level of one or more marker of toxicity (e.g., lyso-SPM) over the course of treatment, thereby indicating an effective treatment regime, or detecting a lack of change in the level of the marker over time, thereby indicating an ineffective regime.

The methods disclosed herein also include methods of treating a human subject having an acid sphingomyelinase (ASM) disorder. In certain aspects, the methods can comprise administering to the subject a first dose of a therapeutic agent for treating an ASM disorder having a first concentration; and administering to the subject a second dose of therapeutic agent having a second concentration equal to or greater than the first concentration if the subject has been determined to have a level of lyso-SPM that is less than or equal to a reference level after administration of the first dose. The methods can include the measurement of lyso-SPM in biological samples from peripheral tissues and the identification of a patient suffering from an ASM disorder by detecting altered lyso-SPM levels. The methods also include monitoring or adjusting a patient's treatment for an ASM disorder by detecting the level of one or more toxicity markers, including lyso-SPM, that are altered as a result of treating the patient with a therapeutic agent, e.g., an agent that reduces the level of SPM in the patient's tissues. The methods allow for the non-invasive evaluation of such patients.

The methods disclosed herein can also be used, in some embodiments, to screen, diagnose, monitor the progression of treatment, and/or adjust treatment for an ASM disorder, such as NPD. For example, the methods include adjusting the dose of a therapeutic agent given to a patient to treat an ASM disorder by measuring a toxicity marker (e.g., lyso-SPM) in order to manage the levels of toxic metabolites resulting from treatment. The methods disclosed herein can be used, in some embodiments, to monitor the long-term efficacy of a course of treatment for an ASM disorder (e.g., if levels of lyso-SPM do not decrease over the course of treatment, this can indicate an ineffective treatment). The methods can also be used, in some embodiments, to screen subjects (e.g., patients who are pre-symptomatic) for elevated lyso-SPM as an initial indication of an ASM disorder. Subjects identified as having elevated lyso-SPM in screening could then be given additional evaluation (e.g., ASM blood testing, genetic testing, etc.) to diagnose/confirm a diagnosis of an ASM disorder, while those subjects who did not exhibit elevated lyso-SPM would not be given additional evaluation. Such a screening method could potentially reducing testing costs.

The methods disclosed herein can include the measurement of lyso-SPM in a biological sample from a human subject and the administration of a therapeutic agent for treating an ASM disorder (e.g., ERT, chaperone therapy, and/or substrate reduction therapy) at optimized concentrations based on the measured level of lyso-SPM. In various embodiments, the biological sample is a peripheral sample. In certain embodiments, the biological sample can be a sample of plasma, whole blood (e.g., dried blood spot), serum, and/or urine. Use of a peripheral sample to measure lyso-SPM levels can avoid the need for invasive procedures such as liver biopsy.

DESCRIPTION OF CERTAIN EXEMPLARY EMBODIMENTS

Figure 1A:
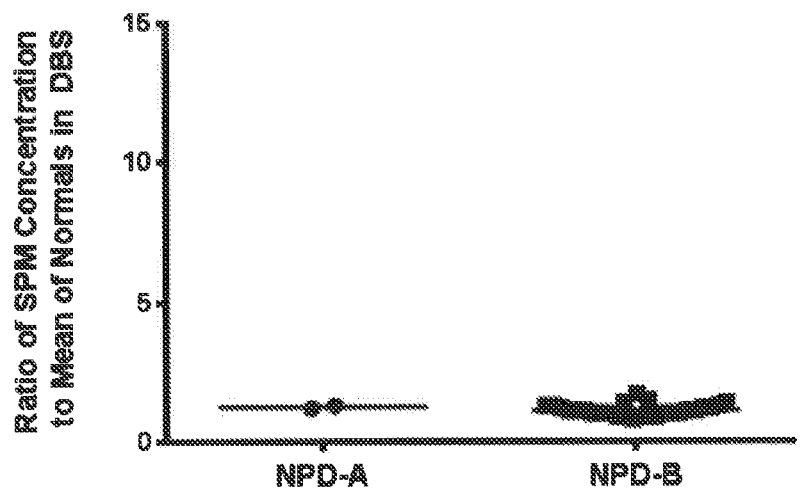
FIG. 1A is a plot showing the ratio of SPM concentration in dried blood spots (DBS) from NPD-A and NPD-B patients to the mean concentration value in DBS from normal control samples.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included," is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Disclosed herein are methods of screening, diagnosing, monitoring the progression of treatment, and/or adjusting the dose of a therapeutic agent for treating an ASM disorder, such as NPD. An "ASM disorder" can encompass any disorder associated reduced expression or impaired function of acid sphingomyelinase. An ASM disorder can also encompass any other disorder associated with accumulation of sphingomyelin in a tissue.

In some embodiments, the methods can comprise administering to the subject a first dose of a therapeutic agent for treating an ASM disorder having a first concentration; and then administering to the subject a second dose of therapeutic agent having a second concentration equal to or greater than the first concentration if the subject has been determined to have a level of lyso-SPM that is less than or equal to a reference (e.g., the level in a sample from a control subject who does not have an ASM disorder, or the baseline level measured in the patient before treatment) level after administration of the first dose.

In certain aspects, the methods comprise collecting and measuring lyso-sphingomyelin (lyso-SPM) in a biological sample from a human subject. The measured level of lyso-SPM can be used to screen, diagnose, monitor the progression of treatment, and/or adjusting the dose of a therapeutic agent for treating an ASM disorder. The methods are based on the discovery that lyso-SPM is significantly elevated in biological samples from peripheral tissues of patients with ASM disorders such as NPD, allowing for the non-invasive evaluation of such patients, including screening for and diagnosing an ASM disorder and monitoring/calibrating/managing therapy for an ASM disorder. The methods are also based on the discovery that the breakdown of accumulated ASM during treatment can lead to elevated levels of markers (e.g., lyso-SPM) that signal the production of toxic or harmful metabolites, and that these harmful levels of metabolites can be avoided by a method of administering a therapeutic agent designed to reduce the levels of SPM (e.g., ERT, chaperone therapy and/or substrate reduction therapy) at doses that prevent excessive metabolite production. The measurement of elevated concentration of lyso-SPM can be used to detect the production of such metabolites and can be used to calibrate therapy to avoid the production of excessively elevated levels of metabolite (e.g., toxic levels). In certain embodiments, the level of lyso-SPM in a patient receiving treatment for an ASM disorder determines whether the dose is increased, decreased, repeated, delayed, or discontinued.

The detection of elevated lyso-SPM levels in a subject having an ASM disorder (e.g., NPD patients) can be used as part of a method of monitoring for an adverse side effect during treatment. For example, the method can comprise collecting a biological sample from the subject, measuring a level of lyso-sphingomyelin (lyso-SPM) in the sample, comparing the measured level of lyso-SPM in the sample to a reference level, and detecting an adverse side effect if the level of lyso-SPM in the sample is elevated. In some embodiments, if the level of lyso-SPM is elevated by a predetermined amount as compared to a reference sample (e.g., a reference level in a sample from a control subject who does not have an ASM disorder), or if the level of lyso-SPM increases by a predetermined amount in the subject over time during the course of treatment (i.e., an increase over the baseline level measured in the patient before treatment, also referred to herein as a reference level), then the measured level of lyso-SPM can be used as an indication of an adverse side effect from the treatment. In some embodiments, the treatment is enzyme replacement therapy (ERT) and the dosage of ERT is managed by collecting one or more biological samples from the patient, testing each sample for an elevation in lyso-SPM, and setting the dose of ERT to a level that does not produce elevated lyso-SPM levels above a predetermined threshold. Managing the dose of a therapeutic agent can include increasing, decreasing, or maintaining the concentration of a therapeutic agent, and/or discontinuing treatment. In certain embodiments, one or more biological samples are collected after a dose of a therapeutic agent is administered and/or just before the administration of a subsequent dose of a therapeutic agent. In some embodiments, an adverse side-effect can be detected if the level of lyso-SPM in the biological sample (e.g., a blood sample such as plasma, serum, or a dried blood spot) is greater than a reference level of about 100-700 ng/ml (e.g., greater than about 100, 200, 250, 300, 400, 500, 600, or 700 ng/ml, or any concentration inbetween), or if the level of lyso-SPM in the biological sample increases by at least about 1.1, 1.5, 2, 2.5, 3, 3.5, 4, 4.5, 5, 5.5, 6, 6.5, 7, 7.5, 8, 8.5, 9, 9.5, or 10 fold, or more (or any value inbetween) over a reference level. For instance, the increase may be at least about 3 fold. The reference level can be, e.g., the level in a sample from a control subject who does not have an ASM disorder or the baseline level measured in the patient before treatment with a dose of the therapeutic agent.

Also disclosed herein are methods of treating a subject having an ASM disorder (e.g., NPD). In various embodiments, the method comprises administering a therapeutic agent for treating an ASM disorder (e.g., ERT, chaperone therapy, and/or substrate reduction therapy) in sequential doses of increasing concentration and monitoring the subject for elevated lyso-SPM levels in a biological sample after each dose (e.g., 1 minute, 5 minutes, 10 minutes, 30 minutes, or 45 minutes, or 1, 2, 3, 4, 5, 10, 12, 15, or 20 hours, or 1 day, 2 days, 5 days, 1 week, 2 weeks, 3 weeks, or 4 weeks after dosing, or any time period in between), or just prior to the next dose. The monitoring of the subject can comprise collecting a biological sample from the subject, measuring the level of lyso-SPM in the sample, comparing the level of lyso-SPM in the sample to a reference level (e.g., the level in a sample from a donor who does not have an ASM disorder, or the level in an ASM patient prior to treatment), and detecting an elevated lyso-SPM level in the sample as compared to the reference level. In some embodiments, the reference level is the level of lyso-SPM measured in a biological sample from a control subject who does not have an ASM disorder. In some embodiments, the reference level is the level of lyso-SPM measured in a sample from the subject taken after the administration of an earlier, lower dose of ERT or before administration of any ERT. In some embodiments, an elevated level of lyso-SPM in the biological sample (e.g., a blood sample such as a serum sample, plasma sample, or dried blood spot) is a level greater than a reference level of, e.g., about 100-700 ng/ml. In some embodiments, an elevated level of lyso-SPM in the biological sample (e.g., a blood sample) is a level greater than a reference level by at least about 1.1, 1.5, 2, 2.5, 3, 3.5, 4, 4.5, 5, 5.5, 6, 6.5, 7, 7.5, 8, 8.5, 9, 9.5, or 10 fold, or more (or any value in between). For instance, the level may be greater by a factor of at least about 3. In some embodiments, a higher concentration dose of ERT is not administered if an elevated level of lyso-SPM is detected after administration of a previous dose.

In addition to monitoring therapy and therapeutic methods, disclosed herein are methods of screening for and/or diagnosing an ASM disorder (e.g., NPD) in a subject. In various embodiments, the method comprises collecting a biological sample from the subject, measuring a level of lyso-SPM in the sample, comparing the level of lyso-SPM in the sample to a reference level, and detecting/diagnosing an ASM disorder if the level of lyso-SPM in the sample is elevated relative to the reference sample. In some embodiments, the reference sample is a sample from a control subject who does not have an ASM disorder. In some embodiments, an ASM disorder can be screened for and/or diagnosed if the level of lyso-SPM in the biological sample (e.g., a blood sample such as a plasma sample, serum sample, or dried blood spot) is higher than a reference level by at least about 1, 1.5, 2, 2.5, 3, 3.5, 4, 4.5, 5, 5.5, 6, 6.5, 7, 7.5, 8, 8.5, 9, 9.5, or 10 fold, or more (or any value inbetween), or higher than a reference level of at least about 200-2000 ng/ml, such as at least about 200 ng/ml, at least about 250 ng/ml, at least about 300 ng/ml, at least about 400 ng/ml, at least about 500 ng/ml, at least about 525 ng/ml, at least about 575 ng/ml, at least about 700 ng/ml, and/or at least about 900 ng/ml (e.g., greater than about 200, 250, 300, 350, 400, 450, 500, 525, 550, 575, 600, 625, 650, 700, 750, 800, 850, 900, 950, 1000, 1050, 1100, 1150, 1200, 1300, 1400, 1500, 1600, 1700, 1800, 1900, or 2000 ng/ml, or any concentration in between). In some embodiments, a biological sample from a normal subject may contain a lyso-SPM level in the range of about 25-200 ng/ml (e.g., about 25, 50, 75, 100, 125, 150, 175, or 200 ng/ml, or any concentration in between).

Measurement of Lyso-SPM

For a discussion of the chemical structure of lyso-SPM, see, e.g., Ito et al., J. Biol. Chem. 270: 24370-4 (1995); see also Caymen Chemical Co. Item Number 10007947, as offered in their catalog.

The methods disclosed herein involve the measurement of lyso-SPM from various biological samples, including samples from peripheral tissues. Any methods for collecting, preparing, and quantifying the level of lyso-SPM from a biological sample can be used. The level of lyso-SPM in a biological sample can be quantified using a spectrometer, such as a mass spectrometer, e.g., LC/MS/MS, or an electromagnetic frequency spectrometer, e.g., UV-VIS, IR, or NMR. In some embodiments, the method of quantifying the level of lyso-SPM can comprise collecting a biological sample (e.g., by arterial or venous puncture, tissue biopsy, buccal swab, urine sample, etc.), detecting and/or separating the lyso-SPM from the other components of the sample (e.g. using an antibody, an indicator chemical, a mass spectrometer such as LC/MS/MS, or an electromagnetic frequency spectrometer such as UV-VIS, IR, or NMR), and comparing the level of lyso-SPM to the level in a reference sample.

Lyso-SPM levels can be measured in biological samples from various tissues with the methods described herein. For example, biological samples from peripheral tissues, such as plasma, whole blood (e.g., dried blood spot), serum, skin, and/or urine can be collected for use in detecting elevated lyso-SPM levels. Biological samples from other tissues can also be used, e.g., spleen, lung, heart, liver, kidney and/or brain tissue. Samples from combinations of two or more tissues can be used (e.g., 2, 3, 4, 5, or more tissues). In some embodiments, the use of a biological sample from a peripheral tissue can avoid the need for invasive procedures such as a liver biopsy.

In some embodiments, the biological sample is subjected to one or more pretreatment steps prior to the detection and/or measurement in the sample of lyso-SPM. In certain embodiments, the sample is pretreated by centrifugation, filtration, precipitation, dialysis, or chromatography, or by a combination of such pretreatment steps. In other embodiments, the sample is pretreated by freezing, chemical fixation, paraffin embedding, dehydration, permeabilization, and/or homogenization, followed by centrifugation, filtration, precipitation, dialysis, and/or chromatography. In certain embodiments, the sample is pretreated by removing cells of a certain type from the sample or removing debris from the sample prior to the evaluation of lyso-SPM.

In various embodiments, the biological sample is evaluated using a device for quantifying or semi-quantifying the level of one or more marker in the sample. For example, the level of lyso-SPM and/or other markers in the sample can be evaluated quantitatively or semi-quantitatively. In some embodiments, a device for quantifying the level of lyso-SPM and/or other markers in a biological sample, such as a tandem liquid chromatography-mass spectrometry (e.g., LC/MS/MS), can be used. In some embodiments, one or more antibodies or other detection agents can be used to bind the lyso-SPM and/or other marker in the biological sample. One or more agents (e.g., a colorimetric agent) can be applied that reacts with the detection agent to emit a detectable signal whose strength, intensity, color, etc. can be used to semi-quantitatively or quantitatively determine the level of lyso-SPM and/or other markers in a sample (e.g., by comparison to the signal from one or more reference samples). Additional methods for quantifying lyso-SPM and/or other markers in a biological sample can also be used, e.g., immunoassays such as ELISA, immunoprecipitation, and western blot, as well as fluorescence-activated cell sorting (FACS), fluorescence resonance energy transfer (FRET), RT-PCR, and/or Northern blot methods.

Managing Treatment of an ASM Disorder

In various embodiments, lyso-SPM levels can be measured as part of a therapy for an ASM disorder. For example, the ASM disorder can be Niemann-Pick disease (NPD), e.g., NPD-A, NPD-B, or NPD-C. The therapy for an ASM disorder can comprise the administration of one or more therapeutic agents that reduces the levels of SPM in the tissues of a patient (e.g., ERT, chaperone therapy, and/or substrate reduction therapy). For example, a within-patient dose-escalation enzyme replacement therapy (ERT) method can be used, such as the ASM dose-escalation methods disclosed in U.S. Application No. 2011/0052559, which is incorporated herein by reference in its entirety (see, for example, paragraphs [0063]-[0075], describing dose escalation protocols).

In various embodiments, a method is disclosed for monitoring a subject for an adverse side effect (e.g., production of toxic or harmful levels of metabolites) by monitoring a marker such as lyso-SPM during a dose escalation therapy for an ASM disorder. The method can comprise collecting a biological sample from the subject, measuring the level of lyso-SPM in the sample, comparing the level of lyso-SPM in the sample to a reference level, and detecting an adverse side effect if the level of lyso-SPM in the sample is elevated as compared to the reference sample. One or more samples can be collected and evaluated after administration of a dose of therapeutic agent, or prior to the administration of the next dose. For example, samples can be collected and evaluated 1 minute, 5 minutes, 10 minutes, 30 minutes, or 45 minutes, or 1, 2, 3, 5, 10, 12, 15, or 20 hours, or 1, 2, 3, 4, 5 days, or 1, 2, 3, or 4 weeks after administration of a therapeutic dose, or any time period in between, or prior to administration of the next dose. In some embodiments, the reference sample is a sample from a control subject who does not have an ASM disorder. In some embodiments, the reference sample is an earlier biological sample from the subject prior to the administration of a higher concentration dose of therapeutic agent (or prior to administration of any therapeutic agent). In some embodiments, if the level of lyso-SPM increases by a predetermined amount or above a predetermined threshold after administration of an initial dose or after administration of an increased (i.e., higher concentration) dose of therapeutic agent (e.g., a higher concentration of ERT), as compared to the level in a reference sample, then this can be used as an indication of an adverse side effect from the treatment. In certain embodiments, if the level of lyso-SPM does not increase or does not increase above a threshold level, then can be used as an indication that an adverse side effect has not occurred.

In various embodiments, a therapy for an ASM disorder is provided. The therapy can comprise the administration of one or more therapeutic agents that reduces the level of SPM in the tissues of a patient (e.g., ERT, chaperone therapy, and/or substrate reduction therapy). In certain embodiments, the therapy can comprise ERT (e.g., ASM replacement therapy). The therapy can comprise monitoring the subject for elevated levels of lyso-SPM during therapy and adjusting the concentration of therapeutic agent (e.g., the concentration of a dose of ERT) to reduce the lyso-SPM levels below a pre-determined threshold level. In some embodiments, monitoring comprises evaluating a sample for elevated levels of lyso-SPM after each dose of therapeutic agent or prior to administration of each subsequent dose of therapeutic agent. In certain embodiments, monitoring after each dose is optional, and is conducted periodically after certain doses of therapeutic agent or prior to administration of certain subsequent dose of therapeutic agent.

In some embodiments, therapy can comprise administering an ERT (e.g., ASM replacement therapy) in sequential doses of increasing concentration, collecting biological samples from the patient after certain doses (e.g., after each dose or prior to each subsequent dose), detecting a level of lyso-SPM in the sample (e.g., using LC/MS/MS), and monitoring the subject for elevated lyso-SPM levels after each dose or prior to administration of the next dose. For example, the biological samples can be collected and monitored for elevated lyso-SPM at 1 minute, 5 minutes, 10 minutes, 30 minutes, or 45 minutes, or 1, 2, 3, 5, 10, 12, 15, or 20 hours, or 1, 2, 3, 4, 5 days, or 1, 2, 3, or 4 weeks after a dose of ERT is administered, or at any time period in between, or prior to administration of the next dose. Monitoring the subject can comprise collecting a biological sample from the subject, measuring a level of lyso-SPM in the sample, comparing the level of lyso-SPM in the sample to a reference level, and adjusting the dose of ERT if the level of lyso-SPM in the sample is elevated by a predetermined amount as compared to the reference sample. In some embodiments, the reference sample is a sample from a control subject who does not have an ASM disorder. In some embodiments, the reference sample is an earlier biological sample from the subject prior to the administration of a higher concentration dose of ERT (or prior to the administration of any ERT). In some embodiments, if the level of lyso-SPM increases by a predetermined amount in the subject sample and/or is higher than a reference threshold, then this can be used as an indication that the ERT dosage should be reduced, delayed, or terminated to avoid the production of toxic or harmful levels of metabolite. In some embodiments, if the level of lyso-SPM is at or below the threshold, than a subsequent dose of equal or higher concentration can be administered.

In various embodiments, a dose escalation therapy is provided, comprising administering ERT to a subject at increasing doses over time to debulk accumulated SPM without producing toxic or harmful levels of metabolite resulting from the rapid hydrolysis of the accumulated SPM. In some embodiments, biological samples from the patient are monitored for elevated levels of lyso-SPM during the dose escalation therapy, as elevated lyso-SPM would indicate the production of toxic or harmful levels of metabolite. In some embodiments, if levels of lyso-SPM above a threshold concentration are detected, or a large increase in lyso-SPM levels as compared to levels in a previous sample are detected, then an increased dose of ERT is delayed or not administered. The ERT can be administered by any route suitable for achieving a therapeutic effect, including intravenously, intradermally, subcutaneously, intraperitoneally, intrapulmonary, topically, intranasally, intracranially, or intramuscularly.

In some embodiments, the ERT can comprise administration of an acid sphingomyelinase (ASM), such as a recombinant human ASM (rhASM), or the ERT can comprise administration of a modified ASM (e.g., modified rhASM). A modified ASM can comprise any modification to the enzyme that does not significantly alter its ability to hydrolyze lysosomal sphingomyelin to ceramide and phosphorylcholine (e.g., the modified ASM exhibits at least about 20, 30, 40, 50, 60, 70, 80, 90, 95, 99, 99.5, or 99.9% of the enzyme activity of unmodified ASM, or any percentage in between). The hydrolytic ability of a modified ASM can be assessed by techniques known to one of skill in the art, such as those described in U.S. Pat. Nos. 4,039,388, 4,082,781, 5,686,240, and 7,563,591, and International Publication Nos. WO 2007/078806 and WO 2006/058385, which are incorporated herein by reference in their entirety.

In some embodiments, the ERT can comprise administration of recombinant human ASM (rhASM) or a modified rhASM. There are various human ASM isoforms known in the art, all of which can be used in the methods disclosed herein. See, e.g., U.S. Application No. 2011/0052559, which is incorporated herein by reference in its entirety (see, e.g., the discussion of human ASM isoforms and enzyme conjugates thereof and their use in ERT at paragraphs [0108]-[0117] and [0124]-[0127]).

In some embodiments, the enzyme replacement therapy is administered to a subject at an initial low, non-toxic dose that is then escalated in subsequent administrations. The highest dose of enzyme that the subject can tolerate without producing toxic or harmful levels of metabolite (as detected by, e.g., monitoring the levels of a toxicity marker such as lyso-SPM) can then be used as a maintenance dose. Alternatively, a therapeutically effective dose less than the highest tolerated dose can be used as a maintenance dose. A therapeutically effective dose can comprise any dose that is sufficient to reduce the concentration of accumulated sphingomyelin in an ASM subject by at least about 5, 10, 15, 20, 25, 30, 35, 40, 45, 50, 55, 60, 65, 70, 75, 80, 85, 90, 95, or 99% (or any percentage in between) after one or more rounds of administration.

Treatment of ASM disorders, such as NPD, require high enough doses of therapeutic agent (e.g., ERT, chaperone therapy, and/or substrate reduction therapy) to achieve adequate distribution of the therapeutic agent in the organs of pathology (e.g., the spleen, lungs, liver, heart, kidney and brain). It has been shown that, following intravenous administration of recombinant human ASM in ASM knockout mice, most of the ASM activity distributes to the liver, with small amounts of ASM enzymatic activity detected in other organs, such as the spleen, heart, liver, kidney and lung. See, e.g., He et al., *Biochimia et Biophsyica Acta* 1432: 251-264 (1999). Thus, doses having an elevated concentration of therapeutic agent (e.g., high concentrations of replacement enzyme) may be required to ensure adequate distribution and delivery to, e.g., the lung, liver, heart and kidney in subjects having an ASM disorder, such as NPD.

Studies in ASM knockout mice have also demonstrated that enzyme replacement therapy may, at sufficiently high doses, result in the production of toxic or otherwise harmful metabolites of sphingomyelin. See, e.g., C. Nickerson, et al., *American Society of Human Genetics* (2005); and J. Murray et al., *Society of Toxicology* (2006). Without being bound by theory, the administration of high doses of ASM to NPD subjects may result in the hydrolysis of large amounts of accumulated sphingomyelin into ceramide and phosphorylcholine. Ceramide is known to play a role in cell death and may be a pro-apoptotic agent. See, e.g., Smith and Schuchman, *FASEB* 22: 3419-3431 (2008). Thus, ceramide may contribute to the toxic side effects observed in the ASM knockout mice and in NPD subjects.

Thus, a calibration and coordination of therapy (e.g., ERT, chaperone therapy, and/or substrate reduction therapy) is needed in order to provide a sufficient concentration of therapeutic agent to debulk and prevent future accumulation of lysosomal sphingomyelin throughout the organs of pathology, while also avoiding the production of excessive concentrations of toxic metabolites. In some embodiments, this coordination is provided through managing a dose-escalation protocol by evaluating the levels of a toxic marker, such as lyso-SPM in a patient sample after certain doses or after every dose and, if necessary, adjusting the dosing regimen as described herein. Managing the dose of a therapeutic agent can include increasing, decreasing, or maintaining the concentration of a therapeutic agent, and/or discontinuing treatment.

In various embodiments, a dose escalation method of treatment involves the administration of one or more initial, low doses of therapeutic agent (e.g., replacement enzyme) to a subject to reduce the amount of sphingomyelin that has accumulated in the subject. The dose of therapeutic agent can then be administered at systematically higher concentrations until the highest dose that is tolerated by the subject and is therapeutically effective is reached. In some embodiments, the therapeutic agent is replacement enzyme (e.g., rhASM) and is administered such that enzyme activity in one or more organs of pathology (e.g., an organ that exhibits elevated lysosomal levels of SPM in a patient suffering from an ASM disorder) is at least about 5%, 6%, 7%, 8%, 9%, 10%, 12%, 15%, 20%, 25%, 30%, 35%, 40%, 50%, 75%, 80%, 85%, 90%, 95% (or any percentage in between) of the activity level of activity in the corresponding organ in a subject who does not suffer from an ASM disorder (e.g., a healthy subject).

In some embodiments, a method of treating an ASM disorder can comprise: (a) administering an enzyme replacement regimen for debulking accumulated sphingomyelin substrate in the subject comprising: (i) administering an initial low dose of rhASM or a modified rhASM to the subject; and (ii) administering successively higher doses of rhASM or a modified rhASM to the subject (dose escalation); (b) monitoring the subject for elevated lyso-SPM levels and/or for one or more additional marker of an adverse side effect after certain doses, or after each dose, administered in steps (a)(i) and (a)(ii) (e.g., using LC/MS/MS to quantify the lyso-SPM concentration); (c) repeating, decreasing, and/or terminating the dose escalation protocol after elevated lyso-SPM levels are detected and/or after one or more additional adverse side effect is detected. In certain embodiments, the method further includes administering a maintenance regimen comprising administering a dose equal to or less than the highest dose tolerated by the subject as the maintenance dose, and optionally further monitoring for elevated lyso-SPM levels during administration of the maintenance regime. In certain embodiments, the initial dose of rhASM or a modified rhASM can range from about 0.03 mg/kg to about 1.0 mg/kg, or about 0.1 mg/kg to about 0.5 mg/kg (the concentration of a dose is measured as mg enzyme to kg body weight). In some embodiments, each subsequent dose of increased enzyme concentration is administered about 1, 2, 3, 4, 5, 6, or 7 days, or 1, 2, 3, 4, or 5 weeks after the previous dose. In some embodiments, the subsequent dose of increased enzyme can be at a concentration of between about 0.1 and 5 mg/kg (e.g., about 0.1, 0.2, 0.3, 0.4, 0.5, 0.6, 0.7, 0.8, 0.9, 1, 1.5, 2, 2.5, 3, 3.5, 4, 4.5, or 5 mg/kg, or any concentration in between).

In some embodiments, a dose of replacement enzyme at a given concentration is administered at least twice (e.g., at least 2, 3, 4, or 5 times) before the next higher concentration dose is administered. In certain embodiments, the successively higher dose can be approximately 0.03 mg/kg, 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.2 mg/kg, 1.5 mg/kg, 1.75 mg/kg, 2 mg/kg, 3 mg/kg, 4 mg/kg or 5 mg/kg higher than the previous dose (or any value in between). In some embodiments, the successively higher dose can be about 0.03 to about 0.1 mg/kg, about 0.1 mg/kg to about 0.5 mg/kg, about 0.5 mg/kg to about 1 mg/kg, about 0.5 mg/kg to about 2 mg/kg, about 1 mg/kg to about 2 mg/kg, about 2 mg/kg to about 4 mg/kg, or about 2 mg/kg to about 5 mg/kg higher than the previous dose (or any value in between). In certain embodiments, the highest dose tolerated by the subject without production of toxic or harmful metabolites can be about 1.0 mg/kg to about 3.0 mg/kg. In some embodiments, the highest tolerated dose is subsequently administered to the human subject as a maintenance dose. In some embodiments, the maintenance dose is administered about every 1 to 8 weeks (e.g., about every 1, 2, 3, 4, 5, 6, 7, or 8 weeks, or any time period in between).

Once a maximum tolerated dosage is identified (e.g., a dose that does not produce toxic or otherwise harmful levels of metabolite), it can be used as a maintenance dose to treat the subject going forward. The maintenance dose can be administered daily, weekly, biweekly, monthly, bimonthly or quarterly (or any time interval in between). Monitoring for elevated lyso-SPM levels can be conducted during administration of the maintenance regime, e.g., 1, 2, 3, 5, 10, 12, 15, or 20 hours, or 1, 2, 3, 4, 5 days, or 1, 2, 3, or 4 weeks after administration of a maintenance dose, or any time period in between. If elevated lyso-SPM levels are detected (e.g., levels greater than a reference level of about 100-700 ng/ml, or levels at least about 1.1-10 fold greater than a reference level), then the maintenance dose can be reduced or discontinued.

Certain other parameters can be measured in combination with lyso-SPM to monitor a subject during therapy (e.g., during ERT) and/or as part of the therapy to determine the maximal dose that can be tolerated by the subject. For example, the subject can be further monitored by measuring SPM levels, plasma ceramide levels, and/or bilirubin concentrations. The subject can also be monitored for the production of "acute phase reactants" and inflammatory mediators that are a measure of inflammatory responses, and/or for other biochemical markers. These other biochemical markers can include, but are not limited to, CRP/ hs-CRP, cytokines (e.g., 1L-8, II-6), calcitonin, and ferritin. In some embodiments, one or more of the parameters listed above can be monitored to ensure a stable response to therapy before elevating the dose to a higher concentration. In some embodiments, the subject can also be monitored for one or more related adverse events, which may include constitutional symptoms (e.g., fever, nausea, vomiting, pain, myalgia and jaundice). Combinations of markers can also be monitored (e.g., lyso-SPM levels in combination with bilirubin and/or ceramide levels can be monitored). Suitable threshold levels for the markers that can be monitored in combination with lyso-SPM are disclosed, for example, in U.S. Application No. 2011/0052559, which is incorporated herein by reference in its entirety (see, for example, paragraphs [0067]-[0086]).

In some embodiments, a subject undergoing a dose escalation protocol (e.g., an ERT dose escalation protocol) is monitored for toxic or harmful side-effects (e.g., by monitoring levels of one or more toxicity markers, such as lyso-SPM) after each round of therapeutic administration (e.g., about 1 minute, 5 minutes, 10 minutes, 30 minutes, or 45 minutes, or 1, 2, 3, 4, 5, 6, 8, 10, 12, 18, or 24 hours, or 2, 3, 4, 5, 6, or 7 days, or 1, 2, 3, or 4 weeks or more after administration, or any time period in between), or prior to administration of a higher concentration of therapeutic agent. In some embodiments, the subject is monitored after each administration of a maintenance dose (e.g., about 1, 2, 3, 4, 5, 6, 8, 10, 12, 18, or 24 hours, or 2, 3, 4, 5, 6, or 7 days, or 1, 2, 3, or 4 weeks or more after administration, or any time period in between), or prior to administration of a subsequent maintenance dose of therapeutic agent. In some embodiments, a subject receives a maintenance dose for one, two, three or more years and is monitored periodically for toxic or harmful side-effects. The monitoring can comprise monitoring the toxicity markers mentioned above, as well as monitoring for related adverse events. If the subject experiences an adverse event or if one or more of the monitored markers indicates a harmful side-effect (e.g., if an elevated level of lyso-SPM is detected), then the administration of the maintenance dose can be terminated or adjusted (e.g., a reduced concentration of ERT can be administered) in order to reduce or minimize the undesirable side-effect.

In various embodiments, a subject can be monitored for a toxic and/or otherwise harmful dose of ERT by measuring lyso-SPM levels from a biological sample obtained after administration of a dose of ERT (e.g., after administration of rhASM or modified rhASM). In some embodiments, the method can comprise collecting a biological sample from the subject, measuring the level of lyso-SPM in the sample, comparing the level of lyso-SPM in the sample to a reference level, and detecting an adverse side effect if the level of lyso-SPM in the sample is elevated as compared to the reference sample or elevated by a particular amount as compared to the reference sample. In some embodiments, the next dose of ERT at a higher concentration is only administered if the level of lyso-SPM in the biological sample is not above a defined threshold after administration of the previous dose. Examples of suitable threshold levels are described herein. In some embodiments, levels of lyso-SPM are also monitored during administration of the maintenance dose. In some embodiments, if the level of lyso-SPM exceeds a defined threshold during administration of the maintenance dose, then the maintenance administration is discontinued or a lower dose is administered that does not result in a level of lyso-SPM above the defined threshold.

In some embodiments, an adverse side-effect of ERT can be detected if the level of lyso-SPM in the biological sample is higher than a predetermined reference level. In some embodiments, an adverse side-effect can be detected if the level of lyso-SPM in the biological sample (e.g., a blood sample) is greater than a reference level of about 100-700 ng/ml (e.g., greater than about 100, 200, 250, 300, 400, 500, 600, or 700 ng/ml, or any concentration inbetween). In some embodiments, an adverse side-effect can be detected if the level of lyso-SPM in the biological sample (e.g., a blood sample) is higher than a reference level by at least about 1.1, 1.5, 2, 2.5, 3, 3.5, 4, 4.5, 5, 5.5, 6, 6.5, 7, 7.5, 8, 8.5, 9, 9.5, or 10 fold, or more (or any value inbetween). For instance, the increase may be at least about 3 fold.

In some embodiments, the methods for treating ASM disorders provided herein reduce spleen volume as assessed by techniques known in the art, e.g., MRI. In certain embodiments, the methods reduce liver sphingomyelin levels as assessed by techniques known in the art, e.g., biochemical analysis and/or histomorphometric analysis of liver samples. In some embodiments, the methods increase exercise capacity as assessed by techniques known in the art, e.g., maximum workload by cycle ergometry, including percent predicted maximum workload, peak oxygen consumption, and/or carbon dioxide production. In some embodiments, the methods increase pulmonary function and/or improve lung clearance, as assessed by techniques known in the art, e.g., DLco, FVC, FEV, and/or TLC. In certain embodiments, the methods decrease bronchial alveolar lavage (BAL) sphingomyelin. In certain embodiments, the methods improve lung appearance as assessed by techniques known in the art, e.g., high resolution CT scan and/or chest X-ray.

In various embodiments, the methods for treating ASM disorders provided herein decrease sphingomyelin concentration in the liver, skin, and/or plasma, and/or reduce serum chitotriosidase, CCL18 levels, lyso-SPM, ceramide, and/or bilirubin. In some embodiments, the methods improve a subject's lipid profile (e.g., decreased cholesterol). In some embodiments, the methods improve one or more neurological function in a subject (e.g., psychomotor function, social responsiveness, etc.). In some embodiments, the methods reduce or ameliorate the severity and/or duration of an ASM disorder and/or one or more symptoms associated with the disorder. In some embodiments, the methods prevent the recurrence of a symptom associated with an ASM disorder. In some embodiments, the methods increase the survival rate of subjects after treatment.

Screening for and/or Diagnosing an ASM Disorder

In various embodiments, disclosed herein are methods of screening for and/or diagnosing an ASM disorder. In some embodiments, the ASM disorder is Niemann-Pick disease (NPD). In some embodiments, the disorder is NPD type A, type B, and/or type C. In some embodiments, an ASM disorder (e.g., NPD) can be screened for and/or diagnosed by measuring lyso-SPM levels in a biological sample taken from a subject.

In some embodiments, a method of screening for and/or diagnosing an ASM disorder in a subject can comprise collecting a biological sample from the subject, measuring the level of lyso-SPM in the sample, comparing the level of lyso-SPM in the sample to a reference level, and detecting/diagnosing an ASM disorder if the level of lyso-SPM in the sample is elevated as compared to the reference level. In some embodiments, a reference level is the level of lyso-SPM measured in a sample from a control subject who does not have an ASM disorder. In some embodiments, an ASM disorder can be detected/diagnosed if the level of lyso-SPM in the biological sample from the subject is higher than a predetermined reference level. In some embodiments, an ASM disorder can be detected/diagnosed if the level of lyso-SPM in the biological sample (e.g., a blood sample) is greater than a reference level of at least about 200-2000 ng/ml, such as greater than about 200 ng/ml, greater than about 300 ng/ml, greater than about 400 ng/ml, greater than about 500 ng/ml, greater than about 525 ng/ml, greater than about 575 ng/ml, and/or greater than about 700 ng/ml (e.g., greater than about 200, 250, 300, 350, 400, 450, 500, 525, 550, 575, 600, 625, 650, 700, 750, 800, 850, 900, 950, 1000, 1050, 1100, 1150, 1200, 1300, 1400, 1500, 1600, 1700, 1800, 1900, or 2000 ng/ml, or any concentration in between). In some embodiments, an ASM disorder can be detected/diagnosed if the level of lyso-SPM in the biological sample (e.g., a blood sample) is greater than a reference level by a factor of about 1-10 fold.

Biological samples from various tissues can be used with the screening and diagnostic methods described herein. For example, biological samples from peripheral tissues, such as plasma, whole blood (e.g., dried blood spot), serum, skin, and/or urine can be used to monitor for elevated lyso-SPM levels. Biological samples from other tissues can also be used, e.g., spleen, lung, liver, heart, kidney and/or brain tissue. Samples from combinations of two or more tissues can be used (e.g., 2, 3, 4, 5, or more tissues). In some embodiments, an ASM disorder (e.g., NPD) can be detected/diagnosed by measuring lyso-SPM levels in a biological sample taken from a peripheral tissue. In certain embodiments, the peripheral tissue can be plasma, whole blood (e.g., a dried blood spot), serum, and/or urine. Use of a peripheral sample can avoid the need for invasive procedures such as a liver biopsy.

In various embodiments, the screening and/or diagnostic methods disclosed herein can further comprise administering a therapeutic agent (e.g., an enzyme replacement therapy) to a subject if an ASM disorder is detected/diagnosed. In some embodiments, the enzyme replacement therapy comprises administering a rhASM or a modified rhASM to the subject.

Kit

In various embodiments, a kit is disclosed herein, comprising a device for collecting a biological sample containing lyso-SPM and/or other markers of an ASM disorder, and instructions to use the kit to measure the level of lyso-SPM and/or other markers in the biological sample. In some embodiments, the device for collecting a biological sample can comprise a test tube, syringe, and/or other container for storing a fluid sample, and/or a test strip, dipstick, etc. Any other device known in the art for collecting a biological sample can also be used. In some embodiments, the biological sample is a sample from a peripheral tissue, such as plasma, whole blood (e.g., dried blood spot), serum, skin, and/or urine. Biological samples from other tissues can also be collected, e.g., spleen, lung, heart, liver, kidney, and/or brain tissue, and the kit comprises a device for collecting a sample from the listed tissues. Samples from a combination of two or more tissues can be used.

In some embodiments, the kit can further comprise a device for measuring the level of lyso-SPM and/or other markers in the biological sample. For example, the kit can include an antibody and/or other detection agents that can be used to detect the lyso-SPM or other markers in the biological sample. In some embodiments, the detection agent is included in or on the tissue collection device (e.g., an antibody or indicator chemical impregnated on a test strip), while in other embodiments, the detection agent is provided separately from the collection device.

In some embodiments, a kit can further comprise a device for quantifying or semi-quantifying the level of lyso-SPM and/or other markers in the sample. For example, an agent (e.g., a colorimetric agent) can be provided that reacts with the detection agent to emit a detectable signal whose strength, intensity, color, etc. can be used to quantitatively or semi-quantitatively determine the level of lyso-SPM and/or other markers in the sample (e.g., by comparison to the signal from one or more reference samples). In some embodiments, the device can comprise a device for separating lyso-SPM from the other components of the sample, e.g., using liquid chromatography and/or mass spectrometry. In some embodiments, the device for quantifying the level of lyso-SPM and/or other markers in the sample is a spectrometer, such as a mass spectrometer, e.g., LC/MS/MS, or an electromagnetic frequency spectrometer, e.g., UV-VIS, IR, or NMR.

In some embodiments, the kit can further comprise instructions to compare the level of lyso-SPM and/or other markers in the sample to a reference level and to detect the presence of toxic levels of one or more metabolites and/or an adverse side effect during a treatment for an ASM disorder if the level of lyso-SPM and/or other toxicity markers in the sample are elevated as compared to one or more reference samples. In some embodiments, the kit can further comprise instructions to compare the level of lyso-SPM in the sample to the level in a reference sample and to screen for and/or diagnose an ASM disorder if the level of lyso-SPM in the sample is elevated as compared to the level in the reference sample.

In some embodiments, the kit can be used as part of a therapy for and/or to diagnose an ASM disorder. In some embodiments, the ASM disorder is NPD-A, NPD-B, or NPD-C.

Subject Populations

In various embodiments, a subject as used herein is a human who is being screened for an ASM disorder. In various embodiments, a subject as used herein is a subject diagnosed with or treated for an ASM disorder in accordance with the methods provided herein is a human who has or is diagnosed as having a disorder that results in excessive accumulation of lysosomal SPM in one or more organ of pathology. In some embodiments, the subject has one or more mutations in the gene encoding acid sphingomyelinase, e.g., a deletion, a frameshift, a missense mutation, and/or a nonsense mutation. In particular embodiments, a subject has NPD. In one embodiment, the subject has NPD-A, NPD-B, or NPD-C.

In some embodiments, a subject has one or more mutations in the SMPD1 gene. In certain embodiments, the mutation is ΔR608 (deletion of arginine 608). In some embodiments, the mutation is a missense mutation. In certain embodiments, the missense mutation is L302P, H421Y or R496L. In other embodiments, the mutation is a deletion that results in the deletion of one, two, three, or more amino acid residues. In specific embodiments, a subject treated for an ASM disorder in accordance with the methods provided herein has one or more of the mutations shown in Table 1 in U.S. Application No. 2011/0052559, which is incorporated herein by reference in its entirety. See also Simonaro et al., *Am. J. Hum. Genet.* 71: 1413-1419 (2002) for mutations in the acid sphingomyelinase gene (designated SMPD1).

In certain embodiments, a subject being screened for or diagnosed with or treated for an ASM disorder in accordance with the methods provided herein may endogenously expresses ASM but with about 2 to 5%, 5 to 10%, 5 to 15%, 5 to 20%, 5 to 30%, 20% to 30%, or 5 to 35% of the activity of normal (e.g., non-mutated) human ASM, e.g., ASM-1. In some embodiments, the subject endogenously expresses ASM with less than 35%, 30%, 25%, 20%, 15%, 10%, 5%, 4%, 3%, 2% or 1% of the activity of normal human ASM, e.g., ASM-1. See, e.g., U.S. Pat. Nos. 4,039,388, 4,082,781, 5,686,240, and 7,563,591, and International Publication Nos. WO 2007/078806 and WO 2006/058385, which are incorporated herein by reference in their entirety, for techniques that can be used to measure the activity of ASM; see also the fluorescence-based, high-performance liquid chromatographic assay described in He et al., *Analytical Biochemistry* 314: 116-120 (2003).

In various embodiments, a subject being screened for or diagnosed with or treated for an ASM disorder in accordance with the methods provided herein may display one or more symptoms of NPD. Symptoms of NPD can include, but are not limited to, a distended abdomen, hepatomegaly, splenomegaly, hepatosplenomegaly, neutropenia, pulmonary disease, lymphoadenopathy, the presence of histochemically characteristic NPD foam cells, anemia (e.g., microcytic anemia), thrombocytopenia, recurrent vomiting, chronic constipation, growth failure (e.g., decreased liner growth and body weight), delayed puberty, recurrent bruising, recurrent bleeding, atherogenic lipid profile (high cholesterol, triglycerides, or LDL, and/or low HDL), pain (headache, back, extremities, abdomen), fatigue, early satiety, low endurance, osteopenia, neurological manifestations, and respiratory difficulties (e.g., interstitial lung disease and/or shortness of breath). Neurological manifestation of NPD include cherry red spot, hypotonia, muscle weakness, psychomotor retardation, spasticity, social unresponsiveness, irritability, and/or seizures.

In certain embodiments, a subject being screened for or diagnosed with or treated for an ASM disorder in accordance with the methods provided herein is a human infant. In other embodiments, the subject is a human child. In certain embodiments, the subject is a human adult (18 years or older). In certain embodiments, the subject is a human female. In other embodiments, the subject is a human male. In certain embodiments, the subject is a human female who is not pregnant or is not breastfeeding.

EXAMPLES

The following examples serve to illustrate, and in no way limit, the present disclosure.

Example 1: Materials and Methods

Whole blood used in the study was acquired from 20 previously diagnosed NPD-B subjects following written informed consent and from 20 healthy adults (purchased from ProMedDx, LLC, Norton, Mass.). Venous blood was drawn into Vacutainer® tubes (Becton, Dickinson and Company, Franklin Lakes, N.J.) containing EDTA, shipped on cold packs overnight, and held at 4° C. Within 48 hours of collection, the blood was mixed by inverting the tubes several times, and 75 μL of blood per spot was spotted onto Whatman 903® specimen collection paper and dried at room temperature for at least 4 hours.

To quantify lyso-SPM, 1-O-hexadecyl-(7,7,8,8-d4)-2-O-acetyl-sn-glyceryl-3-phosphorylcholine (Platelet-activating Factor C16-d4; PAF C16-D4, Cayman Chemical Company, Ann Arbor, Mich.) was used as an internal standard. A 3.2 mm punch of dried blood spots (DBS) was extracted in 200 μL methanol/acetonitrile/water (80/15/5) containing 0.8 ng internal standard, vortexed for 30 minutes, and sonicated for 10 minutes. The eluent was cleared by centrifugation for 5 minutes at 16,200 g and then 30 μL was injected into an API Qtrap 4000 LC/MS/MS (AB Sciex, Toronto, Canada) system interfaced with an Agilent 1100 High Pressure Liquid Chromatography (HPLC) system (Agilent, Palo Alto, Calif.). HPLC was performed with a normal-phase silica column in isocratic mode using a mixture of methanol/acetonitrile/water as the mobile phase. Mass spectrometry (MS) was performed in multiple reaction monitoring (MRM) mode with the following transitions: m/z 465.4>184.1 for lyso-SPM and 528.5>184.1 for PAF C16-D4. To quantitate SPM, C12-SPM (Avanti Polar Lipids, Alabaster, Ala.) was used as the internal standard. The extraction and LC/MS/MS procedures were similar to those used for lyso-SPM except that the eluent was diluted 320-fold before injection and the twelve isoforms of SPM were monitored and summarized.

Example 2: Diagnosis of NPD

Although SPM levels are known to be elevated more than 10-fold in the livers and spleens of NPD-B subjects, SPM levels in the plasma of NPD-B subjects are not appreciably elevated and overlap with those of normal controls. As shown in FIG. 1A, the level of SPM in NPD-A and NPD-B patients was not significantly elevated, as shown by the ratio of SPM concentration in dried blood spots (DBS) from NPD-A and NPD-B patients to the mean concentration value in DBS from normal control samples. SPM is a major component of cell membranes and lipoproteins, and the slight elevation of SPM in DBS from NPD subjects may be related to its already high levels and rapid turnover in the circulation.

Figure 1B:
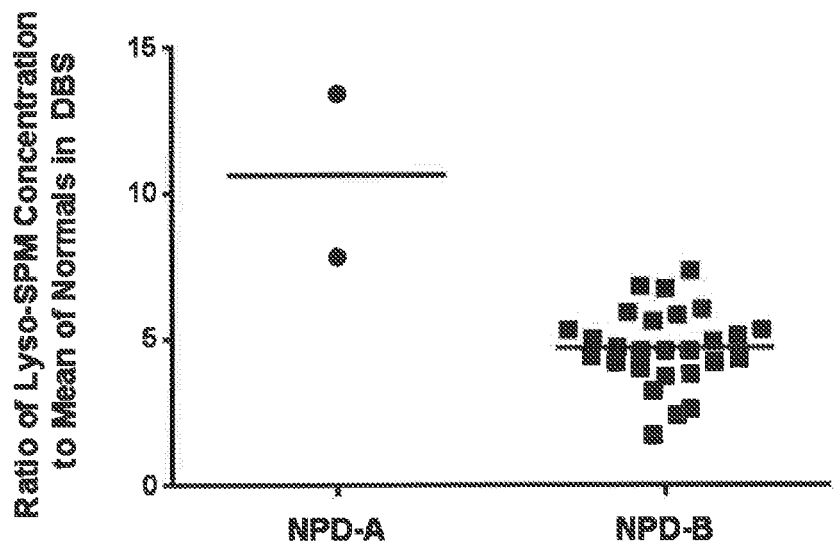
FIG. 1B is a plot showing the ratio of lyso-SPM concentration in DBS from NPD-A and NPD-B patients to the mean concentration value in DBS from normal control samples.

Unlike SPM, lyso-SPM levels were clearly elevated in DBS from NPD-A and NPD-B subjects. As shown in FIG. 1B, the level of lyso-SPM in NPD-A and NPD-B patients was elevated, as shown by the ratio of lyso-SPM concentration in dried blood spots (DBS) from NPD-A and NPD-B patients to the mean concentration value in DBS from normal control samples. The lyso-SPM level did not correlate with the amount of residual ASM activity in DBS or with subject age at collection. In conclusion, lyso-SPM is increased in peripheral tissue (DBS) from NPD subjects at levels that are distinguishable from normal controls.

Example 3: Effect of Dose Escalation in Mouse

Previous studies in ASM knockout mice (Niemann-Pick model mice) demonstrated that clinical symptoms of toxicity were not observed until single doses greater than or equal to 10 mg/kg were used. Nickerson et al., "Dose Responsive Toxicological Findings Following Intravenous Administration of Recombinant Human Acid Sphingomyelinase (rhASM) to Acid Sphingomyelinase Knock-out (ASMKO) Mice," *American Society of Human Genetics* 2005; and Murray et al., "Elevations of Pro-Inflammatory Cytokines and Decreases in Cardiovascular Hemodynamics Following Intravenous Administration of Recombinant Human Acid Sphingomyelinase (rhASM) to Acid Sphingomyelinase Knock-out (ASMKO) Mice," *Society of Toxicology* 2006.

In the current study, ASM knockout mice were administered a single intravenous dose of rhASM at one of three different concentrations: 0 mg/kg, 3 mg/kg (non-toxic dose, no clinically-apparent adverse effects observed), or 20 mg/kg (toxic dose). 3 male and 3 female mice were assigned to each dosage group (18 total animals) and blood samples were collected at the times indicated in Table 1.

TABLE 1

| Group | Treatment | Dose (mg/kg) | Sample Type | Sample Collection Timepoints |
| --- | --- | --- | --- | --- |
| 1 | rhASM | 0 | DBS | 5 minutes and 6, 24, 48, and 72 hours post-dose |
| 2 | | 3 | | 5 minutes and 6, 24, 48, and 72 hours post-dose |
| 3 | | 20 | | 5 minutes and 1, 4, 6, and 9 hours post-dose |

Figure 2:
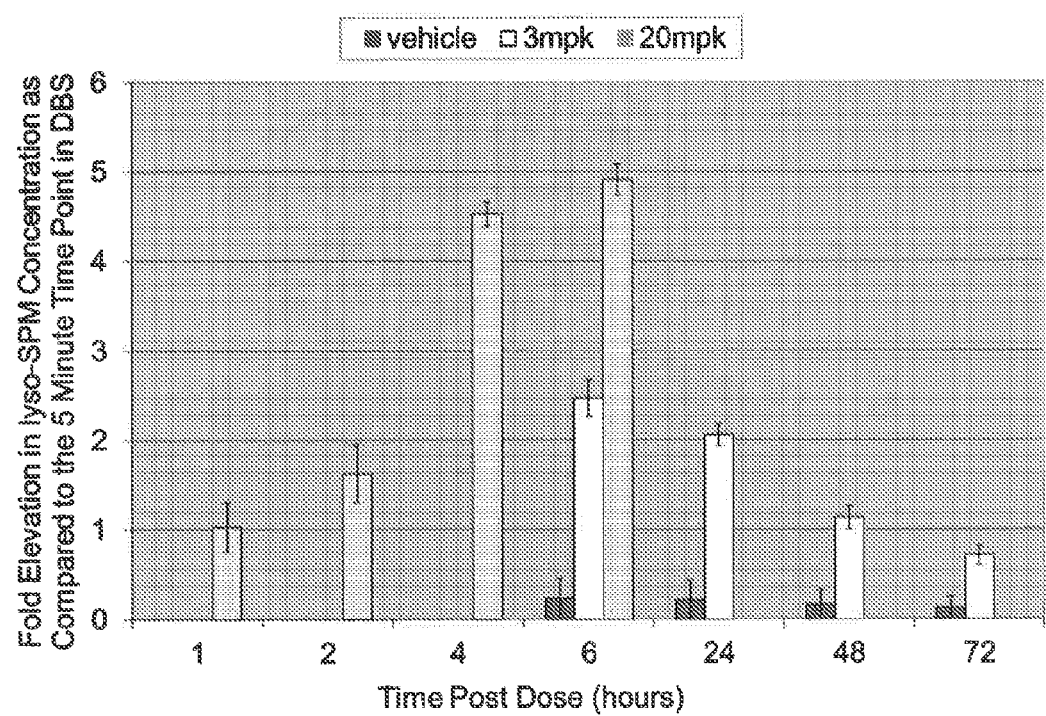
FIG. 2 is a histogram showing the fold elevation in lyso-SPM concentrations (vertical axis) in DBS from ASM knockout mice at the indicated time points (1, 2, 4, 6, 24, 48, and 72 hours post-dose), as compared to the concentration 5 minutes after a single dose administration of 0, 3, or 20 mg/kg rhASM.

Lyso-SPM levels from DBS samples were quantified and showed that levels increased with increasing rhASM dose concentrations, peaking for the 3 mg/kg and 20 mg/kg treatment groups around 6 hours post-dose. See FIG. 2, a histogram showing the fold elevation in lyso-SPM concentrations in DBS for the three doses at the sampled post-dose time points, as compared to the concentration 5 minutes after dosing. Surprisingly, the fold increase in plasma concentration of lyso-SPM in response to a toxic dose (20 mg/kg) of rhASM was markedly higher than the fold increase in plasma concentration of lyso-SPM in response to a non-toxic dose (3 mg/kg) of rhASM. This result suggests that lyso-SPM is useful as a marker for gauging the toxic effects of a therapeutic agent that reduces the level of SPM accumulated in a patient with an ASM disorder.

Example 4: Comparison of Single Dose and Debulking Regimens

Dried blood spots were obtained from wild type (C57BL/6) or ASM knockout (ASMKO) mice following administration of a single dose or a debulking dosing regimen of rhASM. Five ASMKO mice were given a single dose of 10 mg/kg rhASM. Five C57BL/6 and five ASMKO mice were treated using a debulking regimen of 3 mg/kg rhASM and then given a dose of 20 mg/kg. Blood samples were taken at the following time points: 5 minutes, 4 hours, 6 hours, 24 hours, and 72 hours post dose. The animals in the 10 mg/kg dosing group had to be euthanized after the 24 hour time point.

All 70 blood spot samples were prepared using the lipid multiplex extraction procedure and analyzed by LC/MS/MS. Briefly, single DBS spots were punched from each sample card and placed into individual eppendorf tubes. Two hundred microliters of an 80:15:5 solution (MeOH:ACN:H2O) was then added to each tube before it was vortexed for 30 minutes, sonicated 10 minutes, and centrifuged to spin down any particulates. A lyso-SPM calibration curve (without internal standard) was used to determine the concentration of lyso-SPM in each sample.

Figure 3:
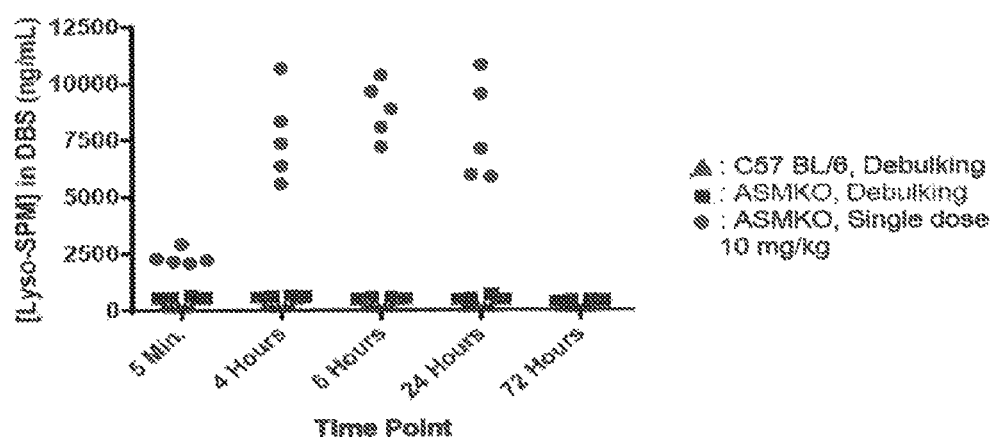
FIG. 3 shows the concentration of lyso-SPM (ng/ml) in DBS obtained from wild type (C57BL/6) or ASM knockout (ASMKO) mice following administration of a single dose (10 mg/kg) or a debulking dosing regimen (3 mg/kg) followed by a dose of 20 mg/kg of rhASM. Blood samples were taken at the following time points: 5 minutes, 4 hours, 6 hours, 24 hours, and 72 hours post dose. The animals in the 10 mg/kg dosing group had to be euthanized after the 24 hour time point.

The data in FIG. 3 show that lyso-SPM levels increased only in the ASMKO group that was treated with a single (high) dose of rhASM at 10 mg/kg, in contrast to the ASMKO group subjected to a debulking regimen. At such a high dose, it is expected that at least 50% of the mice will die between 24 and 72 hours, whereas all mice should survive under the debulking regimen. These results suggest that lyso-SPM could be useful as a marker for gauging the toxic effect of a high dose of a therapeutic agent.

Example 5: Human Testing

Figure 4:
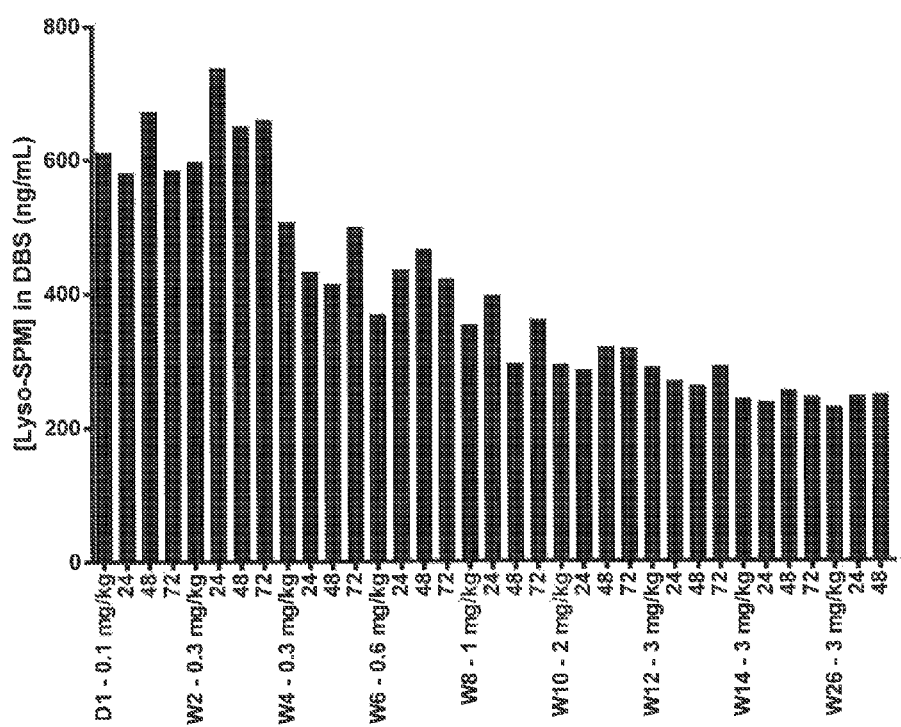
FIG. 4 is a histogram showing the concentration of lyso-SPM (ng/ml) in DBS from a human Niemann-Pick patient collected pre-dose, and 24, 48, and 72 hours after administration of a dose of rhASM over a 26 week period. The doses (0.1, 0.3, 0.6, 1, 2, or 3 mg/kg) and administration date (day 1, week 2, 4, 6, 8, 10, 12, 14, and 26) are indicated on the horizontal axis. At 26 weeks, samples were taken only pre-dose and at 24 and 48 hours post dose.

Blood samples were collected from Niemann-Pick patients being treated with rhASM. A representative example is shown in FIG. 4. Samples were collected pre-dose, and 24, 48, and 72 hours after administration of an indicated dose (0.1, 0.3, 0.6, 1, 2, or 3 mg/kg) of rhASM over a 26 week period (day 1, week 2, 4, 6, 8, 10, 12, 14, and 26). At 26 weeks, samples were taken only pre-dose and at 24 and 48 hours post dose. Levels of lyso-SPM were measured in ng/ml. The data show a general downward trend in lyso-SPM levels following repeated doses at higher concentrations, with fluctuations in the lyso-SPM level between the pre-dose and 72 hour post-dose time points following each individual dose. The earliest post-dose sample was taken after 24 hours, by which time a spike in the lyso-SPM concentration following administration may not have been observed. Administered dosages may also have been below the concentration needed to observe a significant spike in the lyso-SPM level following administration.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A method of treating a human subject having an acid sphingomyelinase (ASM) disorder, comprising:
   (a) administering to the subject a first dose having a first concentration of a therapeutic agent for treating an ASM disorder; and
   (b) administering to the subject a second dose of the therapeutic agent having a second concentration equal to or greater than the first concentration if the subject has been determined to have a level of lyso-sphingomyelin (lyso-SPM) in a peripheral tissue of the subject that is less than or equal to a reference level after administration of the first dose, wherein the peripheral tissue sample is a whole blood, plasma, urine, skin, or serum sample, and wherein the therapeutic agent comprises a recombinant human acid sphingomyelinase (rhASM) or a modified rhASM.

2. The method of claim 1, further comprising repeating the process of steps (a)-(b) at increasing dose concentrations until the subject is determined to have a level of lyso-SPM that is greater than the reference level.

3. The method of claim 2, wherein each dose with successively higher concentration of the therapeutic agent than the previous dose is administered one, two, three, four, five, six, or seven days, or one, two, three or four weeks after the previous dose.

4. The method of claim 2, further comprising administering a maintenance dose of the therapeutic agent, wherein the maintenance dose comprises a concentration equal to or less than the highest concentration of the therapeutic agent tolerated by the subject without detecting a lyso-SPM level that is greater than the reference level.

5. The method of claim 4, wherein the maintenance dose is a therapeutically effective dose of a lower concentration than the highest concentration tolerated.

6. The method of claim 4, wherein the maintenance dose is administered to the subject every two to four weeks.

7. The method of claim 1, wherein determining the level of lyso-SPM in the subject comprises comparing the level of lyso-SPM in a peripheral tissue sample from the subject to the reference level.

8. The method of claim 7, wherein an elevated lyso-SPM level is detected if the level of lyso-SPM in the peripheral tissue sample is at least about 1.1-10 fold greater than the reference level.

9. The method of claim 8, wherein an elevated lyso-SPM level is detected if the level of lyso-SPM in the peripheral tissue sample is at least about 3 fold greater than the reference level.

10. The method of claim 7, wherein an elevated lyso-SPM level is detected if the level of lyso-SPM in the peripheral tissue sample is greater than the reference level which is about 400 ng/ml or about 500 ng/ml.

11. The method of claim 7, wherein the peripheral tissue sample is whole blood.

12. The method of claim 11, wherein the whole blood sample is a dried blood spot.

13. The method of claim 7, wherein an elevated lyso-SPM level is detected if the level of lyso-SPM in the peripheral tissue sample is greater than the reference level which is about 100-700 ng/ml.

14. The method of claim 1, further comprising maintaining the dose, decreasing the dose, or discontinuing administration of the therapeutic agent if the level of lyso-SPM in the subject is determined to be greater than the reference level.

15. The method of claim 1, wherein each dose of the therapeutic agent therapy is administered at least twice.

16. The method of claim 1, wherein the therapeutic agent is administered intravenously, intradermally, subcutaneously, or intramuscularly.

17. The method of claim 1, wherein the ASM disorder is Niemann-Pick disease (NPD) type A, NPD type B, or NPD type C.

18. The method of claim 1, wherein the subject has a mutation in a gene encoding acid sphingomyelinase.

19. The method of claim 18, wherein the mutation is a missense mutation of the acid sphingomyelinase gene.

20. The method of claim 18, wherein the mutation is L302P, H421Y, R496L, or ΔR608.

21. The method of claim 1, wherein the ASM disorder is Niemann-Pick disease (NPD) type B or NPD type C.

22. The method of claim 1, wherein the therapeutic agent is for treating a non-neurological manifestation of the ASM disorder.

23. The method of claim 1, wherein the subject is a human infant or child.

24. The method of claim 1, wherein the subject is a human adult.

25. A method of treating a human subject having an acid sphingomyelinase (ASM) disorder, comprising:
   (a) administering to the human subject a first dose of about 0.03 to about 1.0 mg/kg of a recombinant human acid sphingomyelinase (rhASM) or a modified rhASM;
   (b) comparing the level of lyso-SPM in a peripheral tissue sample from the subject to a reference level, wherein the peripheral tissue sample is a whole blood, plasma, urine, skin, or serum sample;
   (c) administering a second dose of rhASM or modified rhASM having a concentration equal to or greater than the first concentration if the level of lyso-SPM in the peripheral tissue sample after the administration of the first dose of rhASM or modified rhASM is less than or equal to the reference level; and
   (d) repeating the process of steps (a)-(c) at increasing dose concentrations until the level of lyso-SPM after the administration of the dose of rhASM or modified rhASM is greater than the reference level.

26. The method of claim 25, wherein an elevated lyso-SPM level is detected if the level of lyso-SPM in the peripheral tissue sample is at least about 1.1-10 fold greater than the reference level.

27. The method of claim 25, wherein an elevated lyso-SPM level is detected if the level of lyso-SPM in the peripheral tissue sample is greater than the reference level which is about 400 ng/ml or about 500 ng/ml.

28. The method of claim 25, wherein the ASM disorder is Niemann-Pick disease (NPD) type B or NPD type C.

29. The method of claim 25, wherein the rhASM or modified rhASM is for treating a non-neurological manifestation of the ASM disorder.

30. The method of claim 25, wherein the subject is a human infant or child.

31. The method of claim 25, wherein the subject is a human adult.

32. The method of claim 25, wherein the peripheral tissue sample is a whole blood.

33. The method of claim 25, wherein an elevated lyso-SPM level is detected if the level of lyso-SPM in the peripheral tissue sample is greater than the reference level which is about 100-700 ng/ml.

34. A method of treating a human subject having an acid sphingomyelinase (ASM) disorder, comprising:
(a) administering to the subject a first dose having a first concentration of a therapeutic agent, for treating an ASM disorder;
(b) collecting a peripheral tissue sample from the subject, wherein the peripheral tissue sample is a whole blood, plasma, urine, skin, or serum sample;
(c) measuring a level of lyso-sphingomyelin (lyso-SPM) in the peripheral tissue sample;
(d) comparing the level of lyso-SPM in the peripheral tissue sample to a reference level; and
(e) administering a second dose of the therapeutic agent having a concentration equal to or greater than the first concentration if the level of lyso-SPM in the peripheral tissue sample is less than or equal to the reference levels,
wherein the therapeutic agent comprises a recombinant human acid sphingomyelinase (rhASM).

35. The method of claim 34, wherein the ASM disorder is Niemann-Pick disease (NPD) type B or NPD type C.

36. The method of claim 34, wherein the therapeutic agent is for treating a non-neurological manifestation of the ASM disorder.

37. The method of claim 34, wherein the subject is a human infant or child.

38. The method of claim 34, wherein the subject is a human adult.

39. The method of claim 34, wherein the peripheral tissue sample is a whole blood.

* * * * *